(12) United States Patent
Osri

(10) Patent No.: US 9,212,389 B2
(45) Date of Patent: Dec. 15, 2015

(54) VERSATILE THERMAL DETECTION

(76) Inventor: Amots Osri, Beit-hanania (IL)

( * ) Notice: Subject to any disclaimer, the term of this patent is extended or adjusted under 35 U.S.C. 154(b) by 0 days.

(21) Appl. No.: 12/599,696

(22) PCT Filed: Dec. 16, 2007

(86) PCT No.: PCT/IL2007/001552
§ 371 (c)(1),
(2), (4) Date: Dec. 15, 2009

(87) PCT Pub. No.: WO2008/072247
PCT Pub. Date: Jun. 19, 2008

(65) Prior Publication Data
US 2010/0221701 A1    Sep. 2, 2010

Related U.S. Application Data

(60) Provisional application No. 60/869,740, filed on Dec. 13, 2006.

(51) Int. Cl.

| | | |
|---|---|---|
| *C12Q 1/68* | (2006.01) | |
| *C12P 19/34* | (2006.01) | |
| *G01N 33/53* | (2006.01) | |
| *C12M 1/34* | (2006.01) | |
| *G01N 33/00* | (2006.01) | |
| *C07H 21/02* | (2006.01) | |
| *C07H 21/04* | (2006.01) | |
| *A61K 38/00* | (2006.01) | |
| *C07K 1/00* | (2006.01) | |
| *A61K 39/395* | (2006.01) | |
| *A61K 39/00* | (2006.01) | |

(52) U.S. Cl.
CPC .................................. *C12Q 1/6825* (2013.01)

(58) Field of Classification Search
USPC .............. 435/6.1, 6.11, 7.1, 91.1, 183, 283.1, 435/287.1, 287.2; 436/94, 501; 536/23.1, 536/24.3; 530/300, 350; 422/50, 68.1; 424/130.1, 178.1, 184.1; 374/2
See application file for complete search history.

(56) References Cited

U.S. PATENT DOCUMENTS

2005/0196322 A1*  9/2005  Truex et al. ................. 422/82.01
2007/0269821 A1*  11/2007  Mazumdar et al. .............. 435/6

* cited by examiner

*Primary Examiner* — Frank Lu
(74) *Attorney, Agent, or Firm* — Mark David Torche; Patwrite LLC

(57) ABSTRACT

A method of detecting hybridization of complementary segments of nucleic acids by heat generated upon the aforementioned hybridization; a method of detecting the presence of a predetermined reactant in a sample suspected of containing the same, and an apparatus for detecting hybridization of complementary segments of nucleic acids by a heat generated upon aforementioned hybridization, that implements a pyroelectric thermal sensor or a bolometric thermal sensor or a quantum well thermal sensor.

5 Claims, No Drawings

VERSATILE THERMAL DETECTION

This application claims the benefit of U.S. provisional application No. 60/869,740, filed on Dec. 13, 2006 and PCT/IL07/01552, filed on Dec. 16, 2007, now is WO/2008/072247

FIELD OF THE INVENTION

The present invention relates, to detection of various biological and chemical analytes. More particularly, the invention relates to the detection of heat generated upon binding of the reactants associated with the analytes by a matching complementary molecule or alternatively resulting from the metabolic reactions and processes.

BACKGROUND OF THE INVENTION

Various detection techniques and methods based on thermal sensing exist and well-known in the art. Certain methods employ thermocouple, thermopile or infrared sensors, as in U.S. Pat. No. 6,909,093, and in U.S. Pat. No. 6,402,369. Alternatively, some of the methods employ charged coupled devices, as disclosed in U.S. Pat. No. 5,466,348. Several other approaches employ pyroelectric sensors, as in U.S. Pat. No. 4,829,003, and in U.S. Pat. No. 5,108,576.

Thermal sensing is employed in diversified applications and for versatile purposes. Thus, U.S. Pat. No. 4,829,003 discloses a method of detecting enzymes or enzymatic substrates in a liquid or gas stream, by the heat generated upon their interactions, using pyroelectric sensor. U.S. Pat. No. 5,108,576 further suggests employing the pyroelectric sensor for detecting the binding of antigens by antibodies as well as enzyme-substrate and enzyme-coenzyme interactions. Tannenbaum et al., in U.S. Pat. No. 3,878,049 disclose a method for quantitative measurement of concentrations of various reactants, by measuring the heat produced when they metabolized by enzymes or microorganisms.

Various techniques have been used to determine whether a chemical interaction has occurred between two reactants. One example of prior art is the use of micro-cantilevers carrying copies of certain molecule on their tip for detecting possible conjugates in a sample, as disclosed in U.S. Pat. No. 6,203,983. Another example of prior art is the use of fluorescence dyes or other radiative molecules to detect the event of DNA hybridization, or binding between antibodies and their target proteins, disclosed in U.S. Pat. No. 5,578,832, and in U.S. Pat. No. 5,631,734. In these inventions a probe is deposited on a slide and than allowed to hybridize with a sample that carries labeled DNA or proteins. The probe bound labeled molecules are than detected using an optical system.

SUMMARY OF THE INVENTION

The present invention is further described, to demonstrate some of its aspects.

Aspect No 1: This aspect of the present invention relates to the detection of heat generated upon hybridization of complementary segments of nucleic acids. Molecular interactions between two complementary nucleic acid segments is expected to generate change in temperature upon binding; the temperature change can be either exothermic or endothermic and can result from molecular interactions such as binding, for example hybridization of single-stranded DNA molecules, or dissociation of molecules, for example dehybridization of double-stranded DNA molecule. The heat produced can be transmitted by means of conduction, convection, or radiation to a thermal sensor device. The thermal sensor device may be a pyroelectric, a bolometric or a quantum well sensor and uses one or preferably an array of thermal sensor units, preferably arranged in a grid. Each thermal sensor unit is connected to a reading device, has its own specific address and reports the sensed heat to the reading device receiving the data as a change in an electric signal. The sensed heat, for instance, may result from molecular interactions that occur between segments of nucleic acids attached to the device's surface and complementary analytes which are present in an investigated sample; whereby the presence of specific analyte in the sample is detected. Exemplary analytes that can be detected according to this aspect of the present invention include DNA, PNA and RNA.

Aspect No 2: The second aspect of the present invention relates to the detection of heat generated by complex chemical and or physical interactions occurring in biological cells and tissues, typically related to as metabolism. Basically, the second aspect relates to a method and an apparatus employed to detect and decipher multiple events of molecular interactions using thermal sensor device. The thermal sensor device detects the heat generated when binding, association or fusion of several molecules and or molecular complexes occurs and reports it as an electrical signal. The thermal sensing device may be a pyroelectric, a bolometric or a quantum well sensor and uses one or preferably an array of thermal sensor units, preferably arranged in a grid thus allowing spatial resolution. Each thermal sensor unit is connected to a reading device, has its own specific address and reports the sensed heat quantitatively to the reading device receiving the data as a change in an electric signal. Each unit of the thermal sensors array (be it pyroelectric, bolometric or quantum well) is optionally coated directly (or brought into a thermal contact by means of a thermal conducting material) with many copies of the same entity, such as molecule, virion, bacterial or other spore, living cell (be it bacterial, animal, yeast or plant cell), processed or conserved cell (be it bacterial, animal, yeast or plant cell), any cellular fraction, specific organelle, membrane or membrane's fragments, extract from any tissue or cell. While each sensing unit is coated with many copies of the same entity, the array can be made to consist of many units, each coated with a different entity. After coating the array's units with the designated substance it is allowed to react with the analyte (be it solid, gas, liquid, viruses, live cells, suspension or in-vitro or ex-vivo biological material) containing possible conjugates linkable with the substance attached onto the unit or any other material somehow responsive actively with the substance attached onto the unit. Binding, association or fusion events occur between the substance attached onto the unit and matching conjugates or any other material somehow responsive actively with the substance attached onto the unit generate a temperature change (either exothermic or endothermic), which is converted to an electrical signal by the thermal sensors unit. Such application can reveal the onset of reactions in time, in which viruses invade bacteria, animal or plant cells that are placed on the units of the array.

According to some embodiments of the second aspect of the present invention the analyte is initially applied onto the thermal sensor unit and subsequently is triggered or actuated by various means to produce detectable heat; the triggering or actuating means may be for example a specific chemical agent, some biological material, a physical trigger such as electric current or electromagnetic radiation. The thermal sensor units may be used for the detection of naturally occurring chemical, physical, biological or metabolic heat. This is especially useful in various in-vitro, in-vivo and ex-vivo situations. In-vivo situations can include the monitoring of heat response of viruses, bacteria, normal or cancerous biological cells, adipose tissue or ex-vivo liver preparations to specific drugs. The response to immunomodulators can be used for fast drug screening procedures. An array of the invention can also be used to monitor metabolic activity in ex-vivo preparations such as liver slices, muscle preparations, kidney or any other tissue. This allows monitoring of the normal metabolic activity of the tissue under examination and its response to drugs, activation and modulation of metabotrophic pathways and to electrical simulations.

According to some embodiments of the present invention, the analyte and possible conjugates linkable with the analyte or any other material somehow responsive actively with the analyte applied onto the thermal sensor unit in two substantive individual events; whereby, for instance, the onset of viral invasion into bacterial, animal or plant cells can be revealed, by applying initially the invaded cell and subsequently the invading virus or vise-versa.

Aspect No 3: The third aspect of the present invention relates to the employment of bolometric thermal sensors or quantum well thermal sensors for detection of heat generated upon association and or binding of any two molecules that form any type of conjugate. This aspect also covers the possibility of thermal detection of chemical and or biochemical reactions characterized by specificity. This aspect also relates to the above-mentioned applications of the first and the second aspects of the present invention. The employment of the bolometric thermal sensors or quantum well thermal sensors has never been implemented hitherto in the art for the detection of chemical and or biological substances.

The thermal sensor device may use either a bolometric or a quantum well sensor and may use one or preferably an array of thermal sensor units, preferably arranged in a grid. Each thermal sensor unit is connected to a reading device, has its own specific address and reports the sensed heat to the reading device receiving the data as a change in an electric signal. Each unit of the thermal sensors array is optionally coated directly (or brought into a thermal contact by means of a thermal conducting material) with many copies of the same entity such as single or double stranded DNA, PNA or RNA, antibody, peptide, enzyme, co-enzyme, substrate, monomer, polymer or any other type of molecule or substance. While each unit is coated with many copies of one entity, the array can be made from many units, each coated with a different type of entity (such as DNA, antibody, polymer or other).

After coating the array's units with the designated substance it is allowed to react with the analyte, which may be solid, gas, liquid, suspension, of entities such as viruses, living cells, or in-vitro or ex-vivo biological material) containing possible conjugates linkable with the substance attached onto the unit or any other material somehow responsive actively with the substance attached onto the unit. Events of binding, association, fusion or specific reactions occur between the substance attached onto the unit and matching conjugates or any other material somehow responsive actively with the substance attached onto the unit in the analyzed sample generate heat (either exothermic or endothermic), to be converted to an electrical signal by the thermal sensors unit. Upon heating, caused by such events as binding, association, fusion or specific reactions, each unit sends its output to an analog or digital recording device. The recording device identifies the origin of each signal by its address in the array grid. According to some applications of the third aspect of the present invention, the thermal sensor array can be used for detecting naturally occurring metabolic heat. This is also useful in in-vitro, in-vivo and ex-vivo situations in which the sample is placed directly on the sensor. In-vivo situations may include the monitoring of thermal response to viruses, bacteria, normal or cancerous biological cells, adipose tissue or ex-vivo preparations to specific drugs, or immunomodulators, thus allowing fast drug screening process to be applied. According to some other in-vivo situations, the onset of viral invasion into bacterial, animal or plant cells can be revealed accordingly. The array can also be used to monitor metabolic activity in ex-vivo preparations such as liver slices, muscle preparations, kidney or any other tissue. This allows monitoring of the normal metabolic activity of the tissue under examination and its response to drugs, activation and modulation of metabotrophic pathways and to electrical simulations. For instance, these applications combined on one chip can yield complete chemical analyses of a blood sample at once.

Aspect No 4: The fourth aspect of the present invention relates to detection of heat generated by trace amounts of explosive materials. This aspect employs the thermal sensor device for detecting the heat generated when a predetermined molecule reaches the detector and undergoes a specific interaction and or reaction; whereby heat is generated and the thermal sensor device reports it as a change in an electrical signal.

The thermal sensor device may be a pyroelectric a bolometric or a quantum well sensor and has one or preferably an array of thermal sensor units. Each thermal sensor unit is connected to a reading device, has its own specific address and reports the sensed heat to the reading device receiving the data as a change in an electric signal. Each unit of such thermal sensor array (be it pyroelectric, bolometric or quantum well) may be coated directly (or brought into a thermal contact with a thermal conducting material coated with) with many copies of the same entity, such as molecule or molecular complex. Exemplary entities may be antibodies, en enzyme or any other type of molecule or substance. According to this aspect, the entity is characterized by its specific affinity and or specific reactivity towards the molecule of given explosive material. The heat may be produced upon direct interaction and or reaction of the detected molecule, of the explosive material, with the entity or otherwise may be coupled to several other reactions and or processes. While each unit is coated with many copies of only one entity, the array can be composed of many units, each coated with a different type of entity. For instance, the array may contain units covered with recombinant antibodies specific to the molecule of a given explosive alongside units covered with en enzyme that selectively metabolizes the same very molecule; thus the presence of the molecule is detected by two different substantive means. The array is not limited to one type of explosive and versatile array may contain different families of units, each family specialized for detection of a certain molecule of a certain explosive by one or plurality of different substantive means.

After coating the array's units with the designated substance, it is allowed to react with a sample (be it solid, gas or liquid material) containing possible conjugates, substrates, reactants or any other material somehow active towards the unit's attached entity. Binding, association or reaction events occur between the units' attached entity and the matching conjugates, substrates, reactants or any other material somehow active towards the unit's attached entity, in the sample generate heat (either exothermic or endothermic), which is converted to an electrical signal by the thermal sensors unit. Upon binding, association or reaction event each unit sends its output to an analog or digital recording device. The recording device identifies the signal from each unit individually by its address on the array grid. This way the presence of a given explosive in the investigated sample is revealed and reported.

According to some embodiments of the fourth aspect of the present invention, the sample may be collected by an influx of air; thus microscopic particles, aerosols or vapours of the explosive material may be collected and subsequently delivered onto the detector. The air may be filtrated or separated from the microscopic particles or aerosols by various methods known in the art, and material collected from the influx of air may be administrated onto the thermal sensors unit. In case of vapours or gases the influx of air may come in direct contact with the thermal sensors unit.

DISCLOSURE OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Aspect No 1: This aspect of the present invention relates to the detection of heat generated upon hybridization of complementary segments of nucleic acids. Molecular interactions between two conjugates usually generate heat of binding; the heat produced can be either exothermic or endothermic and can result from molecular interactions such as binding, for example hybridization of single-stranded DNA molecules, or dissociation of molecules, for example dehybridization of double-stranded DNA molecule. The heat produced can be transmitted by means of conduction, convection, or radiation to a thermal sensor device. The thermal sensor device may be a pyroelectric, a bolometric or a quantum well sensor and uses one or preferably an array of thermal sensor units, preferably arranged in a grid. Each thermal sensor unit is connected to a reading device, has its own specific address and reports the sensed heat to the reading device receiving the data as a change in an electric signal. The sensed heat, for instance, may result from molecular interactions that occur between segments of nucleic acids attached to the device's surface and complementary segments of nucleic acids which are present in the investigated sample; whereby the presence of specific segment of nucleic acids in the sample is detected. Exemplary analytes that can be detected according to this aspect of the present invention include DNA, PNA and RNA.

The primary object of the preferred embodiment of the present invention is to detect the heat generated upon hybridization of existing DNA or RNA segments present in a given sample with a complementary DNA or RNA segments disposed on the surface of the thermal sensor device.

The object of another embodiment of the present invention is to detect the heat generated by a specific polymerase reaction of de-novo synthesised DNA or RNA segment. For instance, a specific primer disposed on the surface of the thermal sensor device; alongside the introduced sample containing investigated DNA or RNA there are provided nucleotides and a polymerase enzyme; whereby a specific polymerase reaction begins if the investigated sample contains DNA or RNA complementary to the specific primer and whereby the produced heat is used to detect the presence of specific molecules in the sample.

If the amount of heat detected by the sensors, as described above, is extremely small, it can be amplified either by electronic amplifier or by coupling the reaction to a strong exothermic chemical reaction. Alternatively, small heat responses can be detected by improving the signal to noise ratio electronically, or extracted from the noise signal by mathematical means. One method to increase the signal to noise ratio is working in a controlled environment where the temperature, pressure and gas composition (or at least one of these parameters) are known and kept constant, or the environment is shielded from electronic interference by means such as a Faraday cage.

Execution of the first aspect of the present invention is essentially the same for all of the embodiments that fall within the scope of such and characterized by the sequence of steps:
1. Obtaining a crude sample from an individual of interest, for instance cells' homogenate or preferably a body fluid such as: blood, saliva, lymph, urine, or semen. A sample can also be collected from environmental source such as water body or air sample.
2. Preparing the obtained sample by none or more of the following processing steps:
   a. physical homogenization of the sample;
   b. lysis of the cells in the sample;
   c. facilitating or enhancing solubilization of the molecule of interest;
   d. partial purification and or enrichment of the molecule of interest;
   e. concentration of the sample;
   f. formulation of the sample for detection;
   g. optionally, elimination of interferences such as other molecules in the sample that may interfere with detection.

All of the above steps may be modified and or combined with each other to form single substantive procedure. The actual sequence of steps provided above is exemplary.
3. Administering the prepared sample onto a thermal sensor unit of the thermal sensor device.
4. Obtaining the signal in the form of alteration of certain electrical property.
5. Optionally, amplifying the signal, recording the signal, processing the signal, digitizing the signal, enhancing signal to noise ratio.

There are provided below examples of various techniques that may be employed within subsections a-g of abovementioned paragraph No 2.

Preparation of genomic DNA from mammalian tissue, bacteria, and plant tissue starts with some form of cell lysis, followed by removal of proteins and recovery of DNA, followed by purification of DNA by anion-exchange chromatography. Protocols for DNA isolation depends whether the source is mammalian tissue, plant tissue, or bacteria.

Example No 1

To produce DNA from mammalian tissue, the tissue is rapidly frozen and crushed to produce readily digestible pieces. Most of the cellular proteins from the processed tissue are usually degraded by incubation in proteinase K and SDS solution. The digest is deproteinized by successive phenol/chloroform/isoamyl alcohol extractions, recovered by ethanol precipitation, and dried and resuspended in buffer.

Example No 2

To prepare DNA from tissue culture cells their nuclei are extracted, collected, washed, and suspended in hypotonic buffer. The swollen cells are homogenized, and the nuclei pelleted. The cytoplasmic fraction is removed, and nuclei are resuspended in a low-salt buffer. Gentle drop-wise addition of a high-salt buffer then releases soluble proteins from the nuclei without lysing the nuclei. Following extraction, the nuclei are removed by centrifugation, the nuclear extract (supernatant) is dialyzed into a moderate-salt solution, and any precipitated protein is removed by centrifugation.

Example No 3

DNA from plant tissue may be prepared by lysing the tissue with ionic detergent, followed by protease treatment, and subsequently purify the DNA by cesium chloride (CsCl) density gradient centrifugation.

Example No 4

DNA from plant tissue may be prepared by treating the tissue by a series of non-ionic detergent cetyltrimethylammonium bromide (CTAB) to lyse cells, and purify the nucleic acid. Nucleic acid is recovered from the final CTAB solution by isopropanol or ethanol precipitation.

Example No 5

Preparation of bacterial genomic DNA may consist of lysis, followed by incubation with a non-specific protease and a series of extractions prior to precipitation of the nucleic acids. Such procedures effectively remove contaminating proteins, but are not effective in removing exopolysaccharides which can interfere with the activity of enzymes such as restriction endonucleases and ligases. An efficient way to overcome the exopolysaccharides is to follow the protease incubation by a CTAB extraction. The CTAB complexes, with both polysaccharides and residual protein, effectively removing both in the subsequent emulsification and extraction. This procedure is effective in producing digestible chromosomal DNA from a variety of gram-negative bacteria, all of which normally produce large amounts of polysaccharides. If large amounts of clean DNA are required, the procedure can be scaled up and the DNA purified on a CsCl gradient.

Example No 5

Preparation of bacterial plasmid DNA may be performed by variety of techniques exist for the isolation of small amounts of specific plasmid DNA, from miniprep to recovery of DNA fragments from restriction digests/PCR products from agarose gels (with removal of unincorporated nucleoside triphosphates, reaction products, and small oligonucleotides from PCR reactions).

Example No 6

Cytoplasmic RNA from tissue culture cells may be isolated by lysing the cells and denaturing of the cells to liberate total nucleic acids, in the presence of a strong denaturant and deproteinizing agent which inhibits RNase as well as strips the protein away from the RNA. Cells can be lysed by several techniques including:

1. gentle detergent;
2. 4 M guanidinium isothiocyanate;
3. phenol/SDS.

Additional steps are then required to remove the DNA by using, for example, selective precipitation in high salt.

Example No 7

Bacterial RNA—Procedures for isolating RNA from bacteria involve disruption of the cells, followed by steps to separate the RNA from contaminating DNA and protein. Lysis strategies may include chemical degradation of Gram-negative cell walls using sucrose/detergent or lysozyme, and sonication to break open Gram-positive cell walls. Combinations of enzymatic degradation, organic extraction, and alcohol or salt precipitation are employed in the procedures to isolate the RNA from other cellular components, and various inhibitors of ribonuclease activity. If extremely high-quality RNA is required a CsCl step-gradient centrifugation to remove all traces of contaminating DNA may be used.

The first novel aspect of the present invention will be understood and appreciated more fully from the description above taken in connection with the appended illustrative examples.

While the invention is susceptible to various modifications and alternative forms, specific embodiments thereof have been shown by way of example and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

Example No 1

West Nile virus (Flavivirus; WNV) has emerged as a significant agent of arboviral encephalitis that quickly spread through poultry population world wide. WNV is a serious health risk since it may spread to another type of animals and even to human. The current invention can be used to rapidly screen poultry enclosures for WNV infected poultry. In this example, the thermal sensors array includes units covered by oligonucleotide probes encoding for WNV mRNA. Biological sample such as blood, tissue or saliva retrieved from the poultry is hybridized with the array and the presence of WNV is immediately detected allowing the elimination of the infected individuals. This way the spread of the disease through subsequent infections can be halted.

Example No 2

In a similar way, other types of thermal sensors arrays can detect the actual presence or the elevated level of air- or water-born virus or bacteria in real-time or later in a more convenient setting. Units of such arrays can be covered with oligonucleotides specific for viruses or bacteria and hybridized with samples collected from the environment. This can allow for the real time detection of biological threats.

Aspect No 2: The second aspect of the present invention relates to the detection of heat generated by complex chemical and or physical interactions occurring in biological cells and tissues, typically related to metabolism. Basically, the second aspect relates to a method and an apparatus employed to detect and analyze complex events of molecular interactions using thermal sensor devices. The thermal sensor device detects the heat generated when binding, association or fusion of a pair of molecules and or molecular complexes occur and interprets it as an electrical signal. The thermal sensing device may be a pyroelectric, a bolometric or a quantum well sensor and uses one or preferably an array of thermal sensor units, preferably arranged in a grid. Each thermal sensor unit is connected to a reading device, has its own specific address and reports the sensed heat to the reading device receiving the data as a change in an electric signal. Each unit of the thermal sensors array (be it pyroelectric, bolometric or quantum well) is optionally coated directly (or brought into a thermal contact by means of a thermal conducting material) with many copies of the same entity, such as molecule, virion, bacterial or other spore, living cell (be it bacterial, animal, yeast or plant cell), processed or conserved cell (be it bacterial, animal, yeast or plant cell), any cellular fraction, specific organelle, membrane or membrane's fragments, extract from any tissue or cell. While each unit is coated with many copies of the same entity, the array can be made from many units, each coated with a different entity of the same type. Each unit can be of any 2- or 3-dimensional shape. Similarly, the array can also be of any 2- or 3-dimensional arrangements in which the units assume any order in space. The units can be permanently connected to a common supporting material or board, or be added and removed individually from a common board.

After coating the array's units with the designated substance it is allowed to react with the investigated sample (be it solid, gas, liquid, viruses, live cells, or in-vitro or ex-vivo biological material) containing possible conjugates linkable with the substance attached onto the unit or any other material somehow responsive actively with the substance attached onto the unit. Binding, reacting associating or fusing events occur between the substance attached onto the unit and matching conjugates or any other material somehow responsive actively with the substance attached onto the unit generate heat (either exothermic or endothermic), which is converted to an electrical signal by the thermal sensors unit. Such application can reveal the onset of reactions in time, in which viruses invade bacteria, animal or plant cells that are placed on the units of the array.

According to some embodiments of the second aspect of the present invention the investigated sample is initially applied onto the thermal sensor unit and subsequently is triggered or actuated by various means to produce detectable heat; the triggering or actuating means may be for example a specific chemical agent, some biological material, a physical trigger such as electric current or electromagnetic radiation. The thermal sensor units may be used for the detection of naturally occurring chemical, physical, or other metabolic biological heat. This is especially useful in various in-vitro, in-vivo and ex-vivo situations. In-vivo situations can include the monitoring of heat response of viruses, bacteria, normal or cancerous biological cells, adipose tissue, any ex-vivo or tissue preparations to specific drugs. The response to immunomodulators can be used for fast drug screening procedures. An array of the invention can also be used to monitor metabolic activity in ex-vivo preparations such as muscle preparations, liver slices or any other tissue. This allows monitoring of the normal metabolic activity of the tissue under examination and its response to drugs, activation and modulation of metabotrophic pathways and to electrical simulations.

According to some embodiments of the second aspect of the present invention, the analyte and possible conjugates linkable with the analyte or any other material somehow responsive actively with the analyte applied onto the thermal sensor unit in two substantive individual events; whereby, for instance, the onset of viral invasion into bacterial, animal or plant cells can be revealed, by applying initially the invaded cell and subsequently the invading virus or vise-versa.

The second novel aspect of the present invention will be understood and appreciated more fully from the description above taken in conjunction with the appended illustrative examples.

While the invention is susceptible of various modifications and alternative forms, specific embodiments thereof have been shown by way of example and are herein described in detail. It should be understood, however, that the description herein of specific embodiments is not intended to limit the invention to the particular forms disclosed, but to the contrary, the intention is to cover all modifications, equivalents, and alternatives falling within the spirit and scope of the invention.

Example 1

Thermal sensors arrays can also be used for detecting and monitoring the event of viral invasion into bacterial, animal or plant cells. Thus if a unit on the array of the thermal sensor device is coated with live bacterial, animal or plant cells and the investigated sample contains viruses capable of attacking and invading the type of cell the unit coated with, the consequent event of invasion and or membrane fusion may be detected by the heat generated in such process.

Aspect No 3: The third aspect of the present invention relates to the employment of bolometric thermal sensors or quantum well thermal sensors for detection of heat generated upon association and or binding of any two molecules that form any type of conjugate. This aspect also covers the possibility of thermal detection of chemical and or biochemical reactions characterized by specificity. This aspect can also be implemented in the abovementioned applications of the first and the second aspects of the present invention. The employment of the bolometric thermal sensors or quantum well thermal sensors has never been implemented hitherto in the art for the detection of chemical and or biological substances.

The thermal sensor device may use either a bolometric or a quantum well sensor and may use one or preferably an array of thermal sensor units, preferably arranged in a grid. Each thermal sensor unit is connected to a reading device, has its own specific address and reports the sensed heat to the reading device receiving the data as a change in an electric signal. Each unit can be of any 2- or 3-dimensional shape. Similarly, the array can also be of any 2- or 3-dimensional shapes where the units are arranged in any order in space. The units can be permanently connected to a common supporting material or board, or be added and removed individually from a common board.

Each unit of the thermal sensors array is optionally coated directly (or brought into a thermal contact by means of a thermal conducting material) with many copies of the same entity such as single or double stranded DNA, PNA or RNA, antibody, peptide, enzyme, co-enzyme, substrate, monomer, polymer or any other type of molecule or substance. While each unit is coated with many copies of one entity, the array can be made to consist of many units, each coated with a different type of entity (such as DNA, antibody, polymer or other).

After coating the array's units with the designated substance, they are allowed to react with the analyte, which may be solid, gas, liquid, suspension, viruses, living cells, or in-vitro or ex-vivo biological material containing possible conjugates linkable with the substance attached onto the unit or any other material somehow responsive actively with the substance attached onto the unit. Events of binding, association, fusion or specific reactions occur between the substance attached onto the unit and matching conjugates or any other material somehow responsive actively with the substance attached onto the unit in the analyzed sample generate heat (either exothermic or endothermic), to be converted to an electrical signal by the thermal sensors unit. Upon the generation of heat caused by events of binding, association, fusion or specific reactions, each unit sends its output to an analog or digital recording device. The recording device identifies the origin of each signal by its address in the array grid. According to some applications of the third aspect of the present invention, the thermal sensor array can be used for detecting naturally occurring metabolic heat. This is also useful in in-vitro, in-vivo and ex-vivo situations in which the sample is placed directly on the sensor. In-vivo situations may include the monitoring of heat response of viruses, bacteria, normal or cancerous biological cells, adipose tissue or ex-vivo liver preparations to specific drugs, or immunomodulators thus allowing fast drug screening process. According to some other in-vivo situations, the onset of viral invasion into bacterial, animal or plant cells can be revealed. The array can also be used to monitor metabolic activity in ex-vivo preparations such as muscle preparations, liver or any other tissue. This allows monitoring of the normal metabolic activity of the tissue under examination and its response to drugs, activation and modulation of metabotrophic pathways and to electrical simulations.

The second aspect of the present invention will be understood and appreciated more fully from the description above taken in conjunction with the appended illustrative example.

While the invention is susceptible of various modifications and alternative forms, specific embodiments thereof have been shown by way of example and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

Example 1

Thermal sensors arrays can also be used for detecting and monitoring the event of viral invasion into bacterial, animal or plant cells. Thus if a unit on the array of the thermal sensor device is coated with live bacterial, animal or plant cells and the investigated sample contains viruses capable of attacking and invading the type of cell the unit coated with, the consequent event of invasion and or membrane fusion may be detected by the heat generated in such process. This application is especially usefully when the presence of a virus is double-checked or triple-checked; for instance, while one thermal sensor unit may be coated with cells that are potential host for the virus, other thermal sensor unit may be coated with antibody specific for a certain viral protein, other thermal sensor unit may be coated with a DNA or RNA segment complimentary to the viral genome, and other thermal sensor unit may be coated with substrate specific for a certain viral enzyme; whereby the presence of the virus is verified by several independent means.

Aspect No 4: The fourth aspect of the present invention relates to the detection of heat generated by traceable amounts of explosive materials. This aspect employs the thermal sensor device for detecting the heat generated when a predetermined molecule reaches the detector and undergoes a specific interaction and or reaction; whereby heat is generated and the thermal sensor device reports it as a change in an electrical signal.

The thermal sensor device may be a pyroelectric a bolometric or a quantum well sensor and has one or preferably an array of thermal sensor units. Each thermal sensor unit is connected to a reading device, has its own specific address and reports the sensed heat to the reading device receiving the data as a change in an electric signal. Each unit can be of any 2- or 3-dimensional shape. Similarly, the array can also be of any 2- or 3-dimensional shapes where the units are arranged in any order in space. The units can be permanently connected to a common supporting material or board, or be added and removed individually from a common board.

According to some embodiments of the fourth aspect of the present invention, each unit of the thermal sensors array (be it pyroelectric, bolometric or quantum well) may be coated directly (or brought into a thermal contact with a thermal conducting material coated with) with many copies of the same entity, such as molecule or molecular complex. Exemplary entities may be antibodies, enzymes or any other type of molecule or substance. According to this aspect, the entity is characterized by its specific affinity and or specific reactivity towards the molecule of given explosive material. The heat may be produced upon direct interaction and or reaction of the detected molecule, of the explosive material, with the entity or otherwise may be coupled to several other reactions and or processes. While each unit is coated with many copies of only one entity, the array can be composed of many units, each coated with a different type of entity. For instance, the array may contain units covered with recombinant antibodies specific to the molecule of a given explosive alongside units covered with en enzyme that selectively metabolizes the same very molecule; thus the presence of the molecule is detected by two different substantive means.

According to some embodiments related to the fourth aspect of the present invention, the mechanism of detection of the molecule of given explosive material may employ oxidation or other type of reaction induced by a specific catalyst.

According to some embodiments of the fourth aspect of the present invention, a controlled ignition may be employed in order to initiate spontaneous combustion of the molecules of given explosive material; whereby the detected heat is generated upon the combustion of the molecule. According to this embodiment, there is no need for a specific catalyst or receptor. The ignition of the spontaneous combustion may be for example induced by: increasing the pressure; increasing the temperature, an electric current, an electric potential, an electromagnetic radiation, a spark produced by high-voltage discharges between two electrodes separated by a gap, by combination and variation thereof or by any other physical mean.

It should be stressed that the array is not limited to one type of explosive and versatile array may contain different families of units, each family specializing in detection of a certain molecule of a certain explosive by one or plurality of different substantive means.

After coating the array's units with the designated substance it is allowed to react with the investigated sample (be it solid, gas or liquid material) containing possible conjugates, substrates, reactants or any other material somehow active towards the unit's attached entity. Binding, association or reaction events occur between the units' attached entity and the matching conjugates, substrates, reactants or any other material somehow active towards the unit's attached entity, in the sample generate thermal change (either exothermic or endothermic), which is converted to an electrical signal by the thermal sensors unit. Upon binding, association or reaction event each unit sends its output to an analog or digital recording device. The recording device identifies the signal from each unit individually by its address on the array grid. This way the presence of a given explosive in the investigated sample is revealed and reported.

According to some embodiments of the fourth aspect of the present invention, the sample may be collected by an influx of air; thus microscopic particles, aerosols or vapours of the explosive material may be collected and subsequently delivered onto the detector. The air may be filtrated or separated from the microscopic particles or aerosols by various methods known in the art, and material collected from the influx of air may be administrated onto the thermal sensors unit. In case of vapours or gases the influx of air may come in direct contact with the thermal sensors unit.

According to some embodiments of the fourth aspect of the present invention the influx of air may be pressurized and or heated to induce the spontaneous combustion of the molecule of given explosive; moreover, the pressurization and or heating of the air may be combined with a spark produced by high-voltage discharges between two electrodes separated by a gap.

The fourth novel aspect of the present invention will be understood and appreciated more fully from the description above taken in conjunction with the appended illustrative example.

While the invention is susceptible to various modifications and alternative forms, specific embodiments thereof have been shown by way of example and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

Example No 1

A suspected passenger at the airport may be inspected for traces of explosive materials, for instance, by examining the lint at the stitches of his pockets; thus if the suspect has recently carried explosive materials at his pockets, the traces of the explosive material will be collected by the influx of air and delivered into the detector. The molecules of the explosive material then may react with or bind to the entity covering the thermal sensors unit and reveal the presence of a given explosive in the investigated sample.

It will be appreciated by persons skilled in the art that the present invention is not limited by what has been particularly described hereinabove and that numerous modifications, all of which fall within the scope of the present invention, exist. Rather the scope of the invention is defined by the claims which follow:

The invention claimed is:

1. A method of detecting an interaction between a first entity and a second entity, said method comprising:
    attaching at least segments, portions or fragments of said first entity to a surface of a thermal detector;
    preparing a sample to be analyzed, in which said second entity is suspected to be contained in the sample;
    applying said sample onto said surface of said thermal detector, thereby providing for said interaction;
    detecting an electric signal generated by a thermal sensor unit or an array of thermal sensor units of said thermal detector after applying said sample onto said surface of said thermal detector, said detecting said electrical signal consists of measuring the heat of reaction generated by a chemical or biological interaction upon binding, association or fusion of said first entity and said second entity; and
    comparing said electric signal to a predetermined value, the predetermined value including an electric signal generated by said thermal detector when said sample does not contain said second entity, thereby detecting the interaction between said first entity and said second entity.

2. The method as in claim 1, wherein said first entity and said second entity are substantially complementary segments of nucleic acids.

3. The method as in claim 1, wherein two or more different types of said first entity are attached to said surface of said thermal detector.

4. The method as in claim 1, wherein said second entity is at least a portion of a pathogen.

5. The method as in claim 1, wherein said thermal detector is selected from the group consisting of: a pyroelectric thermal sensor, a bolometric thermal sensor, a quantum well thermal sensor, where at least one of said first entity and at least one of said second entity is selected from the group consisting of: a single stranded DNA, single stranded peptide nucleic acid (PNA), single stranded RNA, double stranded DNA, double stranded PNA, double stranded RNA or any combination thereof; or said thermal detector is a pyroelectric thermal sensor, where at least one of said first entity and said second entity is selected from the group consisting of: a single stranded DNA, a single stranded PNA, a single stranded RNA, a double stranded DNA, a double stranded PNA, a double stranded RNA, a peptide, protein, an antibody or any antibody fragment portion of Fab, Fc, Fv, VL, CL, VH or CH, an enzyme, a co-enzyme, a substrate, a monomer or polymer, a virion, a bacterial spore, a living cell, a processed cell, a conserved cell, a cellular fraction, a fraction of cellular extract containing specific organelles, a membrane or membrane fragment, a tissue extract, a cell extract and a structure-specific molecular-recognition artificial molecule.

* * * * *